United States Patent [19]

Suzuki

[11] 4,292,980
[45] Oct. 6, 1981

[54] ELECTRODE ASSEMBLY FOR USE IN ELECTRIC FIELD THERAPY APPARATUS

[75] Inventor: Shotaro Suzuki, Chofu, Japan

[73] Assignee: Hakuju Institute for Health Science Co., Ltd., Tokyo, Japan

[21] Appl. No.: 89,923

[22] Filed: Oct. 31, 1979

[30] Foreign Application Priority Data

Oct. 31, 1978 [JP] Japan .......................... 53-148924[U]

[51] Int. Cl.³ ............................................. A61N 1/04
[52] U.S. Cl. .............................. 128/783; 128/419 N; 361/232
[58] Field of Search ............... 128/804, 783, 798, 799, 128/802, 362, 376–378, 419 R, 419 N, 420 A; 361/232

[56] References Cited

U.S. PATENT DOCUMENTS

| | | | |
|---|---|---|---|
| 752,419 | 2/1904 | Rodrigues | 128/783 |
| 765,470 | 7/1904 | Friedlander | 128/804 X |
| 2,502,865 | 4/1950 | Lund | 128/804 X |
| 2,842,135 | 7/1958 | Browner | 128/802 X |
| 3,750,672 | 8/1973 | Berckheim | 128/376 |
| 3,915,151 | 10/1975 | Kraus | 128/419 R X |
| 4,094,322 | 6/1978 | Hara | 128/419 N |
| 4,119,102 | 10/1978 | LeVeen | 128/804 |

FOREIGN PATENT DOCUMENTS 394385  4/1924  Fed. Rep. of Germany ...... 128/798

*Primary Examiner*—Lee S. Cohen
*Attorney, Agent, or Firm*—Larson and Taylor

[57] ABSTRACT

An electrode assembly for use in electric field therapy apparatus comprises arranging between a pair of opposed electrodes an appropriate number of auxiliary electrodes with a certain distance interposed therebetween and containing all of these electrodes thus arranged in an insulating material, and enables electric field to be applied to a desired sick part of human body to be treated by selectively using pairs of these electrodes and effective electric field therapy to be attained due to the presence of the auxiliary electrodes which serve to prevent the electric field from being diffused.

2 Claims, 6 Drawing Figures

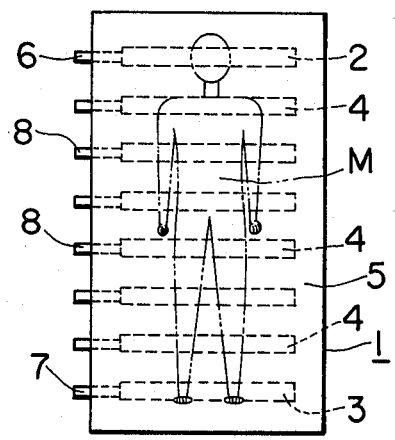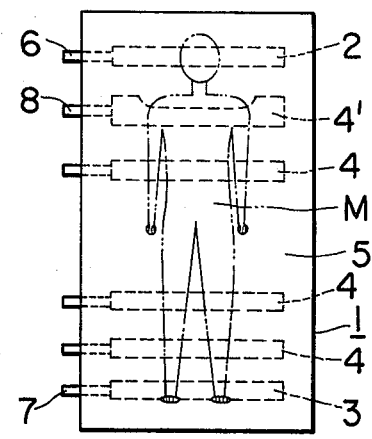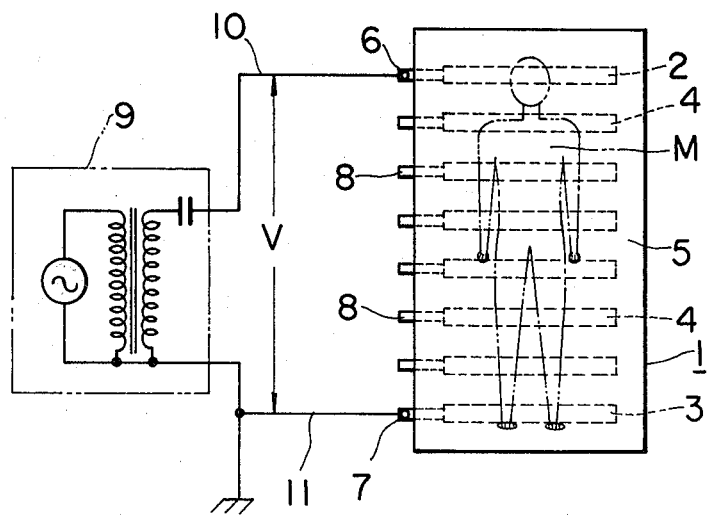

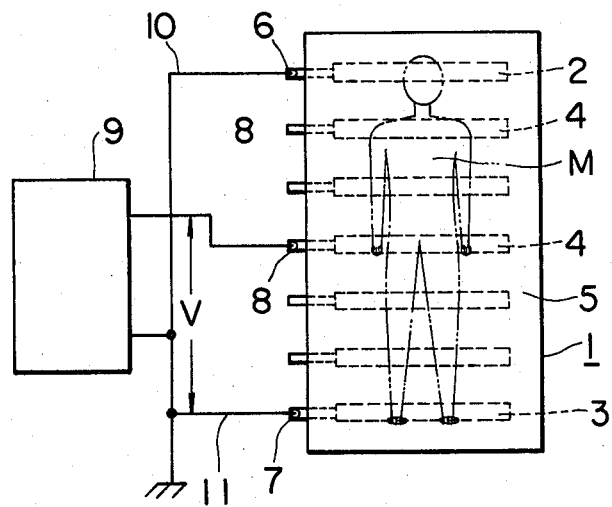
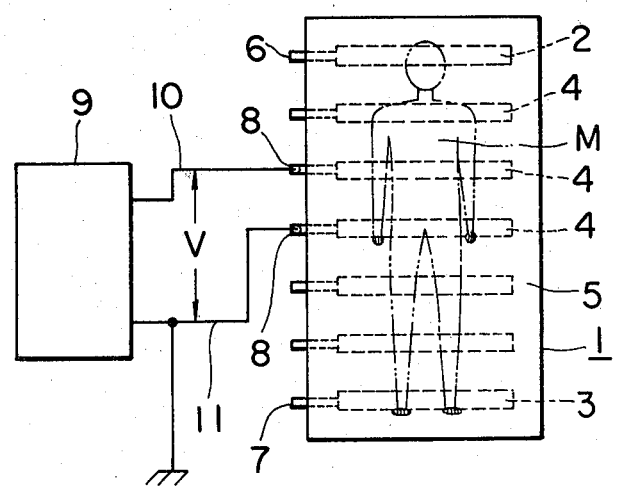

ELECTRODE ASSEMBLY FOR USE IN ELECTRIC FIELD THERAPY APPARATUS

BACKGROUND OF THE INVENTION

The present invention relates to an electrode means for use in therapeutical apparatus designed to treat human body by means of electric field and, more particularly, an electrode means comprising arranging an appropriate number of auxiliary electrodes between a pair of opposing electrodes with a certain distance interposed therebetween and containing these electrodes thus arranged in an insulating material, and capable of focussedly treating a certain sick part of human body by selectively using these electrodes.

Electric field therapy apparatus designed to treat human body in electric field have been widely used as one means to attain physio-therapy and excellent therapeutical effects have been demonstrated. The feature of electric field therapy apparatus exists in that therapeutical treatment can be easily effected all over the human body without current being applied directly to the human body.

Treatment has been effected in the conventional electric field therapy apparatus of this type in such a way that high AC, DC or AC and DC superposed voltage is impressed between a pair of opposing electrodes and that the whole of human body is positioned in the electric field thus formed between the opposing electrodes. This manner of treatment is advantageous to treating the whole of human body, but useless in focussing the electric field to a sick part of human body.

Accordingly, it will be apparent that higher therapeutical effects can be attained when the effect of treating the whole of human body in electric field is further enhanced and at the same time the electric field is focussedly applied only to a sick part of human body. Such a device is now demanded and desired.

SUMMARY OF THE INVENTION

The present invention relates to a new construction of electrode means for use in electric field therapy apparatus and said electrode means comprises arranging an appropriate number of auxiliary electrodes between a pair of opposing electrodes with a certain distance interposed therebetween and containing all of these electrodes in an insulating material, and enables the electric field to be focussedly applied to a sick part of human body by selectively using intended ones of electrodes. Accordingly, this electrode means serves to further enhance the effect of therapy compared to the conventional ones.

An object of the present invention is to provide a new construction of electrode means for use in electric field therapy apparatus.

Another object of the present invention is to provide an electrode means capable of fully treating a sick part of human body by focussedly applying the electric field to that part of human body.

Other object of the present invention is to provide various types of electrode means suitable for treating a sick part of human body.

These and other objects will be apparent from the following detailed description with reference to the accompanying drawings.

BRIEF DESCRIPTION OF THE DRAWINGS

FIG. 1 shows an embodiment of electrode means of the present invention.

FIG. 2 shows another embodiment of electrode means of the present invention.

FIGS. 3 through 5 show how the electrode means shown in FIG. 1 is used.

DETAILED DESCRIPTION OF THE INVENTION

Figure 6:
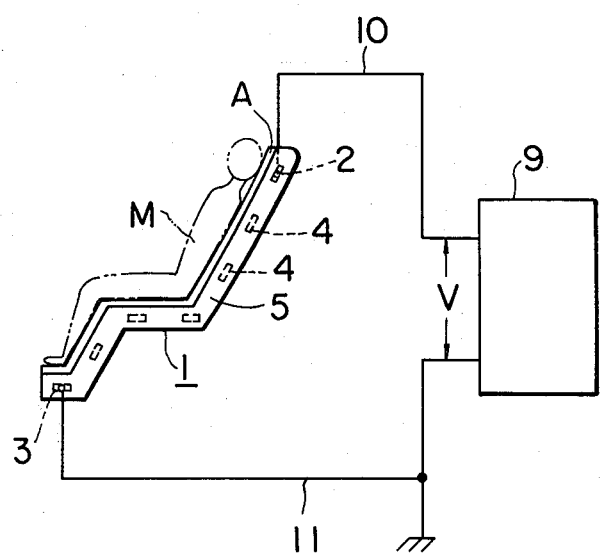
FIG. 6 shows an electrode means of the present invention attached to a chair.

The present invention will be described in detail with reference to the drawings.

FIG. 1 shows an electrode means 1 of the present invention and said electrode means 1 comprises arranging a pair of electrodes 2 and 3 opposite to each other, further arranging between the opposite electrodes 2 and 3 an appropriate number of auxiliary electrodes 4 with a certain distance interposed therebetween, and fixedly containing all of these electrodes in an insulating material 5. Numerals 6, 7 and 8 represent lead terminals of the electrodes 2, 3 and 4, respectively, and symbol M denotes a human body lying on the electrode means 1 to be treated. As shown, the electrodes 2, 3 and 4 all take the form of elongate transversely extending conductors spaced along the length of electrode means.

FIG. 2 shows the most characteristic embodiment of the present invention. In the following Figures same parts as those shown in FIG. 1 are represented by same numerals. In the case of the embodiment shown in FIG. 2, an auxiliary electrode 4′ is designed to have a larger size different from the other ones and the distance interposed between the auxiliary electrodes 4 is arranged to be different from one another, thus enabling electric field to be applied only to a part of the human body to be treated.

FIGS. 3 through 6 show how the examples of the electrode means 1 are used referring only to the example shown in FIG. 1, but the following description can be similarly applied to the example shown in FIG. 2.

In FIG. 3 numeral 9 represents a high voltage generating means which serves in this case to generate high AC voltage and whose insulated lead lines 10 and 11 are connected to the opposed electrodes 2 and 3. The electric field generated by adding AC voltage V between the opposed electrodes 2 and 3 is successively transmitted through the auxiliary electrodes 4. Namely, the electric field is formed between the opposed electrodes 2 and 3 and also between the auxiliary electrodes 4 and 4 and therefore prevented by these auxiliary electrodes 4 from being diffused, thus allowing the efficiency of therapy to be enhanced.

In FIG. 4 the opposed electrodes 2 and 3 are connected each other and AC voltage V is impressed between the opposed electrodes 2, 3 and an auxiliary electrode 4 arranged in the center of the electrode means 1. In the case of FIG. 4 electric field stronger than that in FIG. 3 can be applied to the whole of the human body.

In FIG. 5 high voltage is not impressed between the opposed electrodes 2 and 3, but between an optional pair of the auxiliary electrodes 4, so that the electric field can be applied only to a sick part (belly and its adjacent part in FIG. 5) of the human body M.

FIG. 6 shows a case where therapeutical treatment is effected to the human body M relaxed on a chair A. In this case the electrodes 2, 3 and 4 are arranged along the profile of the chair A to thereby form the electrode means 1.

It will be understood that the arrangement and shape of the electrodes can be varied and that the manner of using the electrodes is not limited to those shown above.

The present invention provides an electrode means for use in electric field therapy apparatus and said electrode means comprises, as described above, arranging the auxiliary electrodes between a pair of opposed electrodes and fixedly containing all of these electrodes in the insulating material, so that electric field can be appropriately applied to the desired sick part of the human body to be treated by selectively using any ones of the electrodes thus arranged. In addition, when electric field is applied to the whole of the human body to be treated, effective electric field therapy can be attained because the electric field is not diffused by the auxiliary electrodes arranged between the opposed electrodes. In other words, the auxiliary electrodes assist in confirming the electric field between the opposed electrodes.

I claim:

1. An electric field therapy apparatus comprising electrode means and a high voltage source, said electrode means including an insulating member on which the body of a patient being treated is received, and a plurality of elongate electrical conductors incorporated in said insulating member and extending transversely to the longitudinal axis of said member, said conductors being spaced apart in serial relationship along the longitudinal axis of said insulating member and being insulated from one another by the insulation of said insulating member, and said apparatus further comprising means for selectively connecting said conductors at least two at a time to said high voltage source such that an electric field is produced between the two connected conductors and the unconnected conductor or conductors located between the at least two connected conductors serve to confine the electric field to an area between the at least two connected conductors.

2. An electric field therapy apparatus designed to produce an electric field for the treatment of a patient, said apparatus comprising electrode means and a high voltage source, said electrode means including an insulating member on which the body of a patient being treated is received, and a plurality of electrically conductive electrodes incorporated in said insulating member, said electrodes being spaced apart in serial relationship along the longitudinal axis of said insulating member and being insulated from one another by the insulation of said insulating member, and said apparatus further comprising means for connecting spaced ones of said electrodes to said high voltage source two at a time so that at least one unconnected electrode is located between the two connected electrodes such that an electric field is produced between the two connected electrodes and the at least one unconnected electrode serves to confine the electricl field to an area between the said two connected electrodes.

* * * * *